United States Patent [19]
Braig et al.

[11] Patent Number: 5,932,877
[45] Date of Patent: Aug. 3, 1999

[54] HIGH PERFORMANCE SIDE STREAM INFRARED GAS ANALYZER

[75] Inventors: James R. Braig, Alameda, Calif.; Daniel S. Goldberger, Boulder, Colo.

[73] Assignee: Square One Technology, Inc., Boulder, Colo.

[21] Appl. No.: 08/842,812

[22] Filed: Apr. 17, 1997

[51] Int. Cl.$^6$ .......................... A61B 5/097; G01M 21/35
[52] U.S. Cl. ................ 250/343; 250/339.13; 250/252.1; 600/532; 73/23.3
[58] Field of Search ............................... 250/343, 339.13, 250/252.1; 600/532; 73/23.3

[56] References Cited

U.S. PATENT DOCUMENTS

| | | |
|---|---|---|
| 3,725,658 | 4/1973 | Stanley et al. . |
| 4,177,381 | 12/1979 | McClatchie et al. . |
| 4,297,871 | 11/1981 | Wright et al. . |
| 4,558,708 | 12/1985 | Labuda et al. . |
| 4,692,621 | 9/1987 | Passaro et al. . |
| 4,852,583 | 8/1989 | Walker . |
| 5,081,998 | 1/1992 | Yelderman et al. . |
| 5,095,915 | 3/1992 | Engelson . |
| 5,247,185 | 9/1993 | Herrera et al. . |
| 5,281,817 | 1/1994 | Yelderman et al. . |
| 5,282,473 | 2/1994 | Braig et al. ............................. 128/664 |
| 5,296,706 | 3/1994 | Braig et al. . |
| 5,464,982 | 11/1995 | Drucker et al. ......................... 250/343 |
| 5,583,339 | 12/1996 | Black et al. ........................ 250/339.13 |

*Primary Examiner*—Constantine Hannaher
*Assistant Examiner*—Andrew Israel
*Attorney, Agent, or Firm*—Woodcock Washburn Kurtz Mackiewicz & Norris, LLP

[57] ABSTRACT

An side stream infrared gas analyzer for detecting the concentration of a gaseous component of a substantially gaseous flow stream such as the expired air of a patient under anesthesia. The infrared gas analyzer comprises an infrared energy detector, a sample cell, and an infrared energy source which are designed to be small and to consume relatively little electrical power. The infrared energy detector converts the received incident radiation into at least one electrical signal representative of the received incident radiation and is preferably mounted directly onto a printed circuit board containing signal processing circuitry which processes the electrical detection signals provided by the infrared energy detector. The infrared energy detector also has a first infrared transmissive window on a detection side thereof through which the incident radiation passes for detection. The sample cell is preferably mounted on the detection side of the infrared energy detector and receives at least a portion of the substantially gaseous flow stream from the patient and directs the received portion to a detection volume which shares the first infrared transmissive window of the infrared energy detector on one side thereof. The infrared energy source is then mounted on the side of the sample cell opposite the infrared energy detector so that emitted infrared energy passes through a second infrared transmissive window which is shared by the infrared energy source and a side of the detection volume opposite the infrared energy detector. After passing through the second infrared transmissive window, the infrared energy from the infrared source passes through the detection volume for absorption by the gaseous component and then through the first infrared transmissive window for detection by the infrared energy detector. The concentration of the gas constituent is then calculated from the resulting absorption signal.

11 Claims, 6 Drawing Sheets

HIGH PERFORMANCE SIDE STREAM INFRARED GAS ANALYZER

BACKGROUND OF THE INVENTION

1. Field of the Invention

The present invention relates to a high performance side stream infrared gas analyzer which continuously determines the concentration of predetermined constituents (e.g., $CO_2$ and $N_2O$) of the respiratory gases of a patient. In particular, the present invention relates to a side stream infrared gas analyzer which can be mounted directly onto a printed circuit board without additional mechanical components and which is configured such that the infrared transmissive windows of the detector and the infrared source also serve as respective windows on the sample cell for containing the gas stream for analysis.

2. Description of the Prior Art

It is frequently of critical importance to monitor the concentrations of carbon dioxide ($CO_2$) and nitrous oxide ($N_2O$) in the gases inspired and expired from a patient under anesthesia, for expired $CO_2$ and $N_2O$ concentrations are reliable indicators of the carbon dioxide and nitrous oxide concentrations in the arterial blood. In a clinical setting, monitoring expired $CO_2$ and $N_2O$ prevents malfunctions in anesthesia rebreathing apparatus from going undetected and delivering excessive amounts of $CO_2$ or $N_2O$ to the patient. Rebreathing of anesthetic gases is very cost effective and environmentally desirable, but accurate $CO_2$ and $N_2O$ concentrations are difficult to maintain in the patient's bloodstream without a concentration monitor.

It is known by those skilled in the art that directing infrared radiation through a sample of a gaseous mixture and measuring the incident radiation illuminating a detecting device on the other side of the sample will provide a measure of the infrared absorption of the gas. Electrical signals produced by such a detecting device are indicative of the infrared absorption of the gas and can be processed to produce an output indicating the concentration of one or more of the constituents of the gas being analyzed. This type of gas analyzer operates on the principle that various gases exhibit substantially increased absorption characteristics at specific wavelengths in the infrared spectrum and that higher gas concentrations exhibit proportionally greater absorption.

Infrared respiratory gas analyzers for use in critical care applications come in two pneumatic configurations, namely, mainstream and side stream. A mainstream analyzer is placed in the patient's respiratory circuit and measures the absorption of infrared light transmitted through the patient's inspired and expired respiratory gases as they flow through the respiratory circuit. Such a mainstream infrared gas analyzer is described in detail by Yelderman et al. in U.S. Pat. Nos. 5,081,998, 5,095,913 and 5,281,817 assigned to the present Assignee and hereby incorporated by reference in their entirety. These applications describe an infrared detector and a shutterless optically stabilized capnograph which has no moving parts, which does not require a modulated source of infrared radiation, and which does not suffer from thermal drift. The disclosed infrared detector includes a substantially identical pair of thermopile detectors mounted on the same ceramic substrate and connected in series opposition. Because of this configuration, balanced and equal incident radiation illuminating the pair will produce no signal. Also, because the reference junctions of both detectors are on the same ceramic substrate and at substantially the same temperature, a drift in substrate temperature will produce no discernible change in output signal. In order to make the system respond to incident radiation, a blocking filter is placed over one of the thermopile detectors in the pair. With the filter in place, the system responds to incident radiation but is substantially insensitive to other thermal changes since the effect of a variation in background signals is compensated by subtracting the outputs of the two thermopile detectors. Conventional side stream analyzers, on the other hand, draw a small, continuous sample of the respiratory gases through a fixed sample cell and out through an exhaust port of the sample cell. The side stream analyzer measures the absorption of infrared light as it is transmitted through the sample cell. Typically, a side stream analyzer requires a pneumatic sample system which incorporates pumps, tubing and fittings. The sample system may also require valves, flow controls, pressure controls and moisture filters or separation devices. For example, a simple configuration which uses a pump to supply the sample gas to the sample cell is illustrated by Passaro et al. in U.S. Pat. No. 4,692,621. Since conventional mainstream infrared gas analyzer configurations take advantage of the primary flow of the respiratory gases, they do not require the additional complexity of a pneumatic system such as those used in prior art side stream infrared gas analyzer configurations.

A mainstream infrared gas analyzer of the type described in the aforementioned Yelderman et al. patents requires the optical and electronic components to be physically connected to the patient's airway or respiratory circuit. As a result, a mainstream gas analyzer may be subjected to mechanical abuse and temperature variations when in use. A side stream configuration, on the other hand, allows the optical components to be remotely located from the patient's respiratory circuit so that the optical and electronic components (i.e., the optical bench) can be protected by a fixed, temperature controlled housing. Thus, while a mainstream configuration has the advantage of reduced complexity, side stream configurations are often desired since they have the advantage of protection from damage and thermal gradients.

Conventional side stream optical benches use infrared detectors which must be stabilized by mechanical chopping techniques. As just noted, conventional side stream optical benches also require accurate temperature control of the detector environment to assure stability. For example, such a conventional side stream infrared gas analyzer is disclosed by McClatchie et al. in U.S. Pat. No. 4,177,381. McClatchie et al. therein describe an infrared gas analyzer which utilizes mechanical choppers and temperature controllers in their measurements. McClatchie et al. also utilize a sample cell which directs the air therein so as to prevent direct impingement of oils, particulate matter, and other contaminants onto the infrared transparent windows so as to prevent contamination of the windows. Unfortunately, this system is quite complex and expensive and relatively unreliable because of the numerous mechanical elements.

A simpler, more reliable side stream gas analyzer has been developed by the present inventors. Prior art FIG. 1 illustrates a cutaway view of a side stream infrared gas analyzer 100 of the type described in U.S. Pat. No. 5,282,473, also assigned to the present Assignee and hereby incorporated by reference in its entirety. The prior art side stream infrared gas analyzer 100 includes a sample cell 101, an infrared source (not shown), and an infrared detector 102 mounted in opposite housing halves 104 so that their optical axes are aligned with respect to the sample cell 101. As shown, housing halves 104 include a clearance 106 for accommodating the infrared source and a separate cavity 108 for accommodating the infrared detector 102. As illustrated, the infrared detector 102 may comprise a plurality of constituent selective filters 109 in a plurality of constituent channels including a reference channel. Optical funnels 110 and 112 are included in the respective housing halves 104 to reduce the optical apertures of the infrared source and the infrared detector 102 at the windows 114 and 116 disposed on ledges 118. The walls of the optical funnels 110 and 112 are treated by plating or painting a thin layer of gold over a nickel plating so that the optical funnels 110 and 112 are highly reflective at the infrared wavelengths output by the infrared source. In addition, the gas passageway into the sample cell 101 is shaped to create smooth transitions from the round cross-section at the gas tube inlet connection from the patient's airway to the rectangular cross-section at the aperture 120 where the gas passageway intersects the optical path to define the detection volume within the sample cell 101.

While the side stream gas analyzer 100 of prior art FIG. 1 significantly decreases the optical path length and significantly improves the response time and signal levels of the device, a smaller and less cumbersome side stream gas analyzer is desired which does not require optical funnels 110 and 112 and which uses even less electrical power. Ideally, such a side stream gas analyzer is configured so that it is small and compact enough to be mounted directly onto a printed circuit board without requiring additional mechanical components. The present invention has been designed to meet these needs in the art.

SUMMARY OF THE INVENTION

The above-mentioned and other needs in the art have been met by a low cost, low power, small, yet high performance gas analyzer in a side stream configuration. The device is based on the technology developed by the present inventors in U.S. Pat. Nos. 5,095,913, 5,081,998, 5,281,817, 5,247,185, and 5,296,706 and the principles of NDIR spectroscopy; however, unlike prior art devices which are typically larger and more cumbersome and use more parts making them less efficient and more costly, the device of the present invention is small and consumes relatively little electrical power. Indeed, it is an object of the invention that the device be small enough that it can be mounted directly onto a printed circuit board with no additional mechanical components.

Another object of the invention is that the infrared transmissive window of the detector also serves as a window on the sample cell for containing the gas stream from the patient's airway. Prior art devices use two separate windows, one on the detector package and one on the sample cell to contain the gas sample. A single window is desired to streamline the design (e.g., an optical funnel as in U.S. Pat. No. 5,282,473 is unnecessary), to make the device more optically efficient because fresnel reflection losses from multiple surfaces are reduced, and to reduce cost. Similarly, it is desired that the infrared transmissive window of the light source also be used to contain the sample gas so that only one window is needed on the source side of the sample cell.

Yet another object of the invention is that the gas sample path be very smooth and of low swept volume so that the sample gas may traverse the sample path quickly so as to reduce pneumatic response time. As noted in U.S. Pat. No. 5,282,473, such smooth transitions of the sample cell tend to promote laminar flow which is preferred over turbulent flow for faster pneumatic response time.

Still another object of the invention is that the light source completely fills the detector's field of view so that the device will be more optically efficient whereby the light source can operate at lower temperatures and power levels.

A further object of the invention is that the gain of each preamplifier channel of the detector's signal processing circuitry can be set independently and permanently by simply adjusting the position of a jumper on the circuit board.

A still further object of the invention is that calibration coefficients for the analyzer are stored in a memory, such as an Electrically Programmable Read Only Memory (EPROM), on the circuit board on which the analyzer is mounted so that the calibration information cannot be separated from the analyzer.

These and other objects and advantages are met in accordance with the invention by providing an infrared gas analyzer for detecting the concentration of a gaseous component of a substantially gaseous flow stream comprising an infrared energy detector, a sample cell, and an infrared energy source which are designed with the above objects in mind. In a preferred embodiment of the invention, the infrared energy detector converts received incident radiation into at least one electrical signal representative of the received incident radiation and has a first infrared transmissive window on a detection side thereof through which the incident radiation passes for detection. The sample cell is preferably mounted on the detection side of the infrared energy detector and receives at least a portion of the substantially gaseous flow stream from the patient and directs the received portion to a detection volume which shares the first infrared transmissive window of the infrared energy detector on one side thereof. The infrared energy source is then mounted on the side of the sample cell opposite the infrared energy detector so that emitted infrared energy passes through a second infrared transmissive window which is shared by the infrared energy source and a side of the detection volume opposite the infrared energy detector. The emitted infrared energy then passes through the detection volume for absorption by the gaseous component and through the first infrared transmissive window for detection by the infrared energy detector. Preferably, the infrared energy detector is, in turn, mounted directly onto a printed circuit board containing signal processing circuitry which processes the electrical detection signals provided by the infrared energy detector.

In a preferred embodiment of the invention, the signal processing circuitry includes amplifier circuitry for each output channel of the infrared energy detector, and the amplifier circuitry for each channel includes an adjustable connection whereby the gain of each channel is set independent of the gain of each other channel. Preferably, the signal processing circuitry also includes a memory device, such as an EPROM, containing calibration coefficients for accounting for differential absorption effects of the infrared energy detector, sample cell, infrared energy source, and the first and second infrared transmissive windows.

In the preferred embodiment of the invention, the detection volume of the sample cell is designed to have a smooth surface and a low swept volume which promotes laminar flow of the gaseous flow stream through the sample cell. The infrared energy source is further mounted on the sample cell opposite the infrared energy detector so as to completely fill the field of view of the infrared energy detector. A reflective insert may be located within the sample cell to improve the optical efficiency of the detection volume. In addition, the infrared energy source may be enclosed in a housing which is coated, painted, and/or plated with a reflective material so that a discrete energy reflector is not necessary. Ideally, the infrared energy source is clamped by a clamp and held in place within the housing so that it is adjacent the second infrared transmissive window.

The scope of the invention also includes a method of manufacturing an infrared gas analyzer which detects the concentration of a gaseous component of a substantially gaseous flow stream provided via an airway. A preferred embodiment of the manufacturing method of the invention comprises the steps of:

mounting an infrared energy detector onto a circuit board containing signal processing circuitry which processes electrical signals output by the infrared energy detector in response to received incident radiation;

mounting a sample cell on a detection side of the infrared energy detector such that the sample cell and the infrared energy detector share a first infrared transmissive window through which the incident radiation passes for detection, whereby the sample cell, when mounted, receives at least a portion of the substantially gaseous flow stream and directs the portion to a detection volume of the sample cell which shares the first infrared transmissive window of the infrared energy detector on one side thereof; and mounting a source of infrared energy on a side of the sample cell opposite the infrared energy detector such that the infrared energy source and the sample cell share a second infrared transmissive window through which infrared energy from the infrared energy source passes into the detection volume for absorption by the gaseous component.

Preferably, the infrared energy source mounting step includes the step of mounting the infrared energy source on the sample cell opposite the infrared energy detector so as to completely fill a field of view of the infrared energy detector. The infrared energy source mounting step may also include the step of clamping the infrared energy source within a housing such that the infrared energy source is adjacent the second infrared transmissive window.

The preferred manufacturing method of the invention also includes the further step of setting a gain of each output channel of the infrared energy detector independent of a gain of each other output channel by adjusting an adjustable connection in amplifier circuitry in the signal processing circuitry for each output channel. The signal processing circuitry is then calibrated using calibration coefficients stored in a memory, such as an EPROM, in the signal processing circuitry on the circuit board.

BRIEF DESCRIPTION OF THE DRAWINGS

The above and other objects and advantages of the invention will become more apparent and more readily appreciated from the following detailed description of the presently preferred exemplary embodiment of the invention taken in conjunction with the accompanying drawings, of which.

DETAILED DESCRIPTION OF THE PREFERRED EMBODIMENT

A system and method which meets the above-mentioned objects and provides other beneficial features in accordance with the presently preferred exemplary embodiment of the invention will be described below with reference to FIGS. 2–9. Those skilled in the art will readily appreciate that the description given herein with respect to those figures is for explanatory purposes only and is not intended in any way to limit the scope of the invention. All questions regarding the scope of the invention should be resolved by referring to the appended claims.

Figure 1:
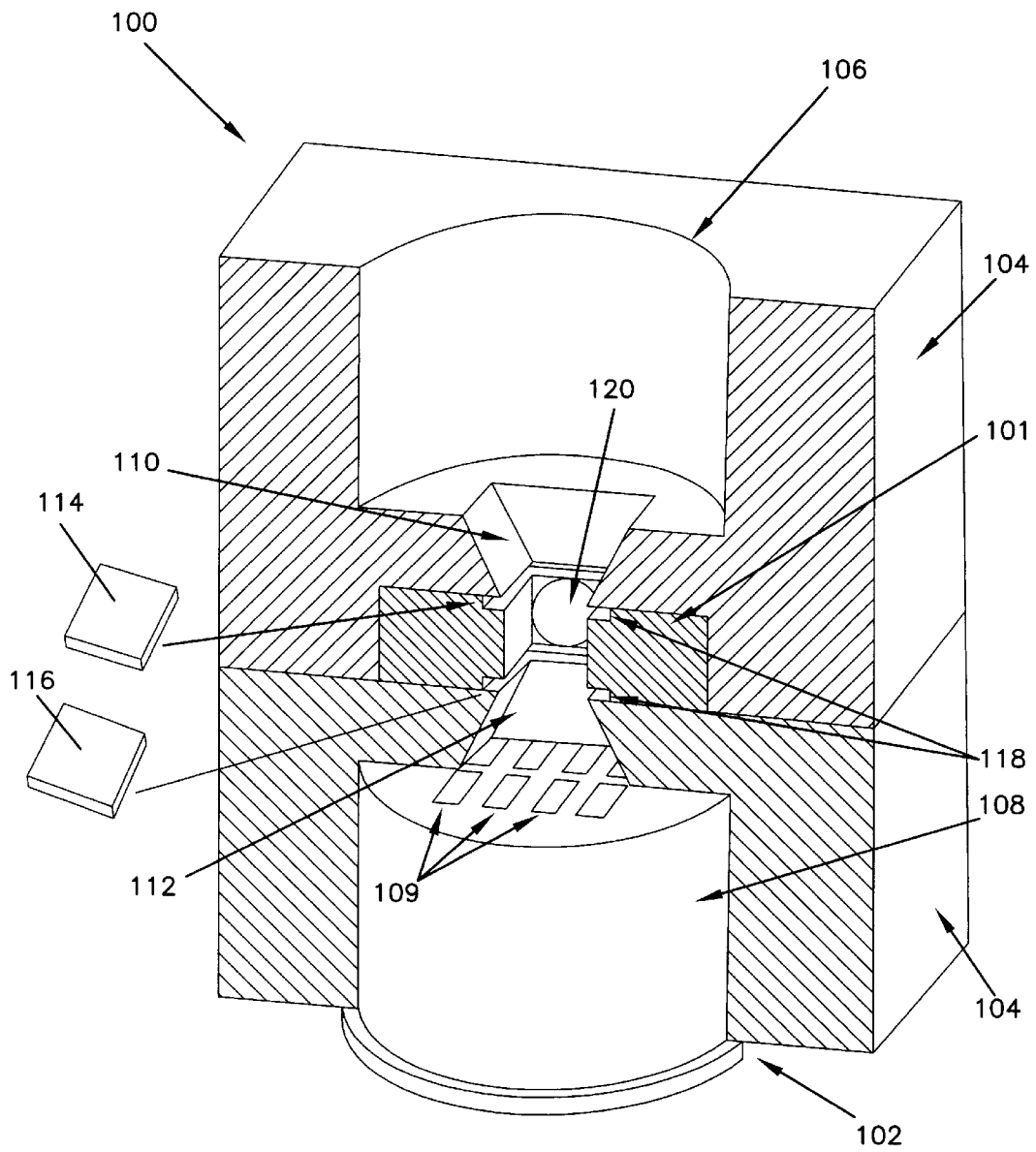
FIG. 1 illustrates a cutaway view of the prior art side stream infrared gas analyzer described in U.S. Pat. No. 5,282,473.
Figure 2:
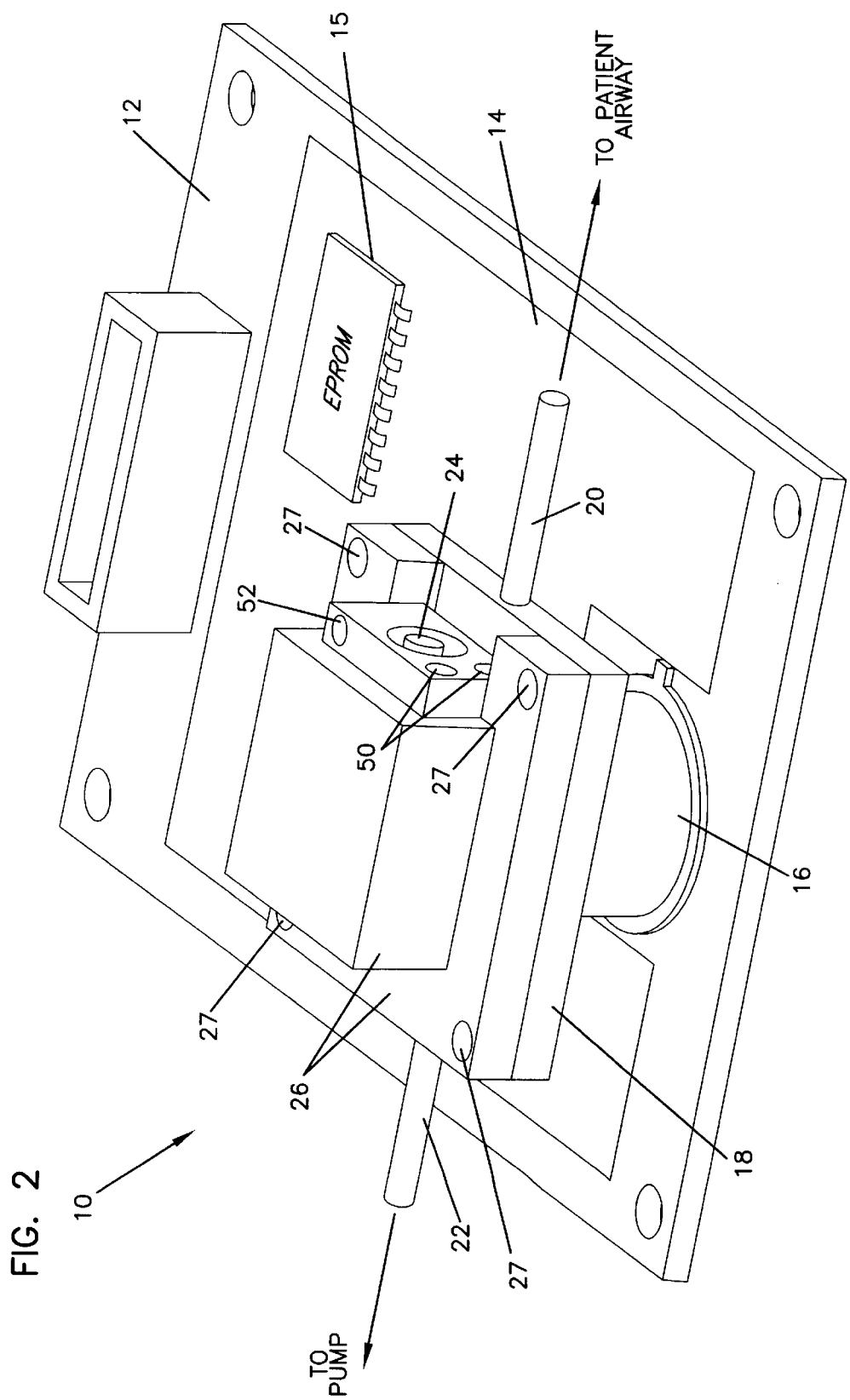
FIG. 2 illustrates an isometric view of a preferred embodiment of a side stream infrared gas analyzer in accordance with the invention.

FIG. 2 is an isometric, diagrammatic view of a preferred embodiment of the side stream infrared gas analyzer 10 of the invention. As shown, the side stream infrared gas analyzer 10 of the invention is mounted on a printed circuit board (PCB) 12 which includes signal processing circuitry 14 etched and mounted on the PCB 12 in accordance with known techniques. Signal processing circuitry 14 processes the electrical infrared detection signals from the infrared gas analyzer 10 to yield the gas concentration signals. Preferably, the signal processing circuitry 14 includes an EPROM 15 which is physically mounted on PCB 12 so that the calibration information stored therein cannot be separated from the infrared gas analyzer 10. In accordance with the preferred embodiment of the invention, the infrared energy detector 16 is mounted directly on the PCB 12 and soldered to form the desired mechanical and electrical connections. Preferably, the infrared detector 16 is of the type described in U.S. Pat. No. 5,081,998 by the present inventors, although other detector technologies may be used.

A sample cell or sensor body 18 (FIGS. 4–6) is mounted directly to the housing of the infrared energy detector 16 in a gas tight manner. Epoxy can be used to create such a gas tight, mechanically sound connection. Although not shown, a reflective insert can be located within the sample cell 18 so as to improve the optical efficiency of the detection cavity. Alternatively, the interior walls of the sample cell 18 can be coated, painted, and/or plated with a reflective material such as a thin layer of gold over a nickel plating A tube fitting 20 from the patient's airway and a tube fitting 22 to a pump are respectively located in the inlet and outlet ports of the sample cell 18 to facilitate pneumatic connections. The tube fittings 20 and 22 may be type 304 S/S hypo tubing HTX-16-6 or equivalent which are secured and sealed in place by a gap filling, cyanoacrylate cement. Alternatively, tube fittings 20 and 22 can be fabricated and/or formed as an integral part of the sample cell 18, e.g., by injection molding.

Figure 3:
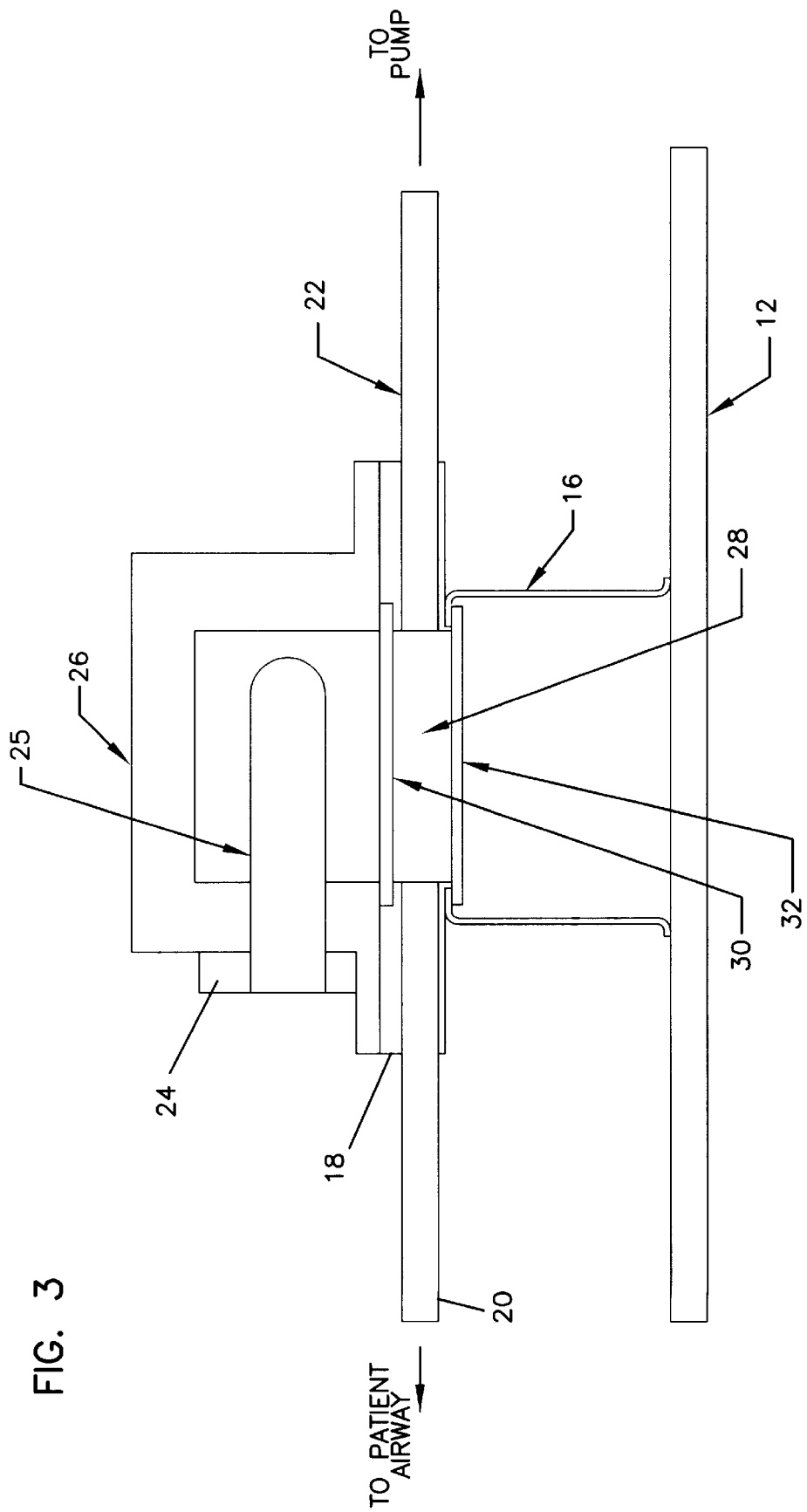
FIG. 3 illustrates a side cutaway view of the side stream infrared gas analyzer of FIG. 2.

As better illustrated in FIG. 3, a heater clamp 24 (FIGS. 7 and 8) clamps an infrared energy source 25 so that it is retained within a receptacle in the housing 26 of the infrared energy source 25. In a preferred embodiment, infrared energy source 25 is a regulated infrared energy source of the type described in U.S. Pat. No. 5,247,185, although other infrared sources such as a filament source sold commercially by Ion Optics or its equivalent may also be used. As illustrated in FIG. 2, housing 26 is mounted to sample cell 18 via mounting screws placed in recesses 27, while the heater clamp 24 is mounted to the housing 26 via mounting screws placed in recesses 50 and 52. Preferably, the infrared energy source 25 is clamped by heater clamp 24 such that it is disposed adjacent detection volume 28 within sample cell 18. In addition, a reflector (not shown) may be located in housing 26 and retained by locating a hub 48 of the heater clamp 24 (FIG. 8) in its receptacle in the housing 26. Alternatively, the inside surface of the housing 26 can be coated, painted, and/or plated with a reflective material eliminating the need for the discrete reflector. The resulting infrared energy source assembly is thermally efficient because heat conduction paths are limited to a small area at the distal end of the infrared energy source 25. Conduction losses are further minimized by selecting materials with a low coefficient of thermal conductivity.

Figure 4:
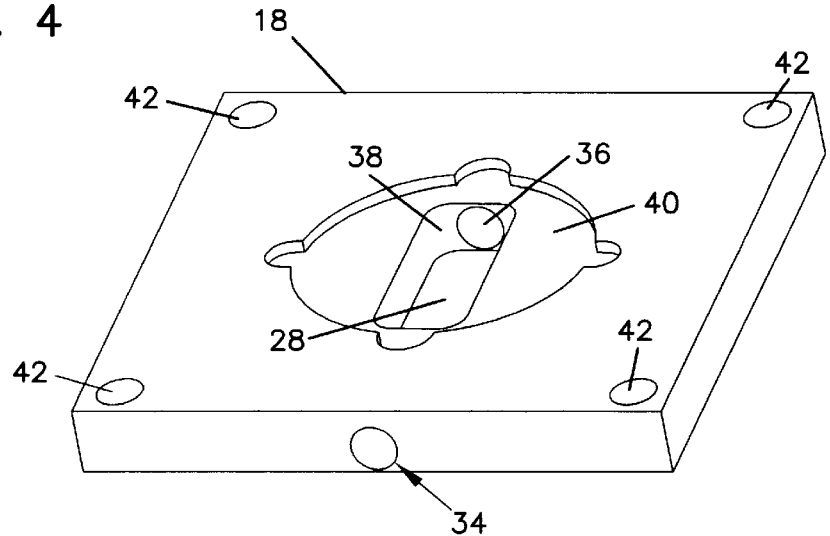
FIG. 4 illustrates a perspective view of the bottom of the sample cell of the invention.
Figure 5:
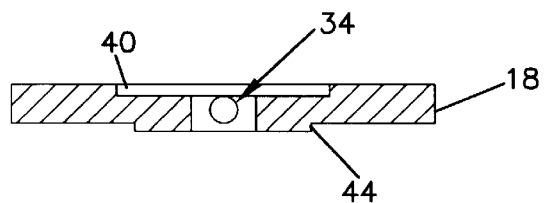
FIG. 5 illustrates a side view of the sample cell of the invention.
Figure 6:
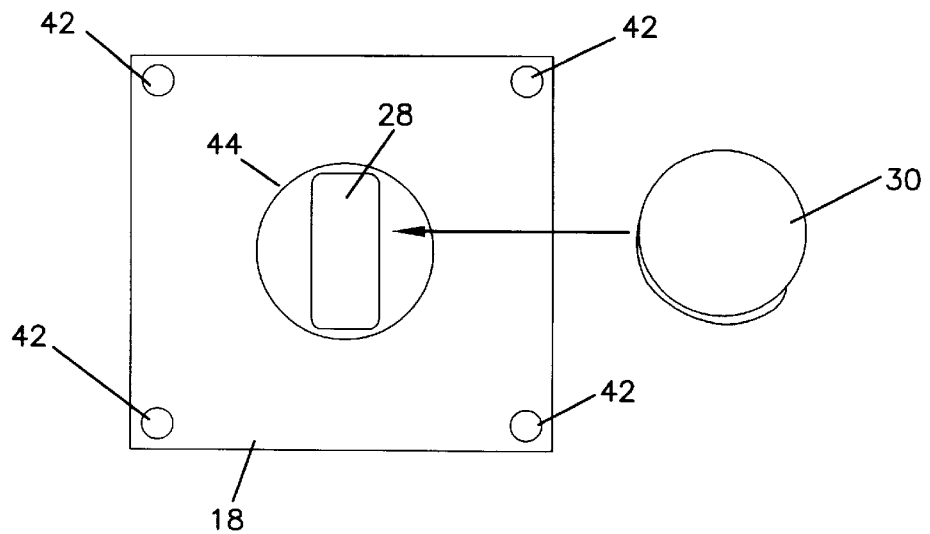
FIG. 6 illustrates a top view of the sample cell of the invention.
Figure 7:
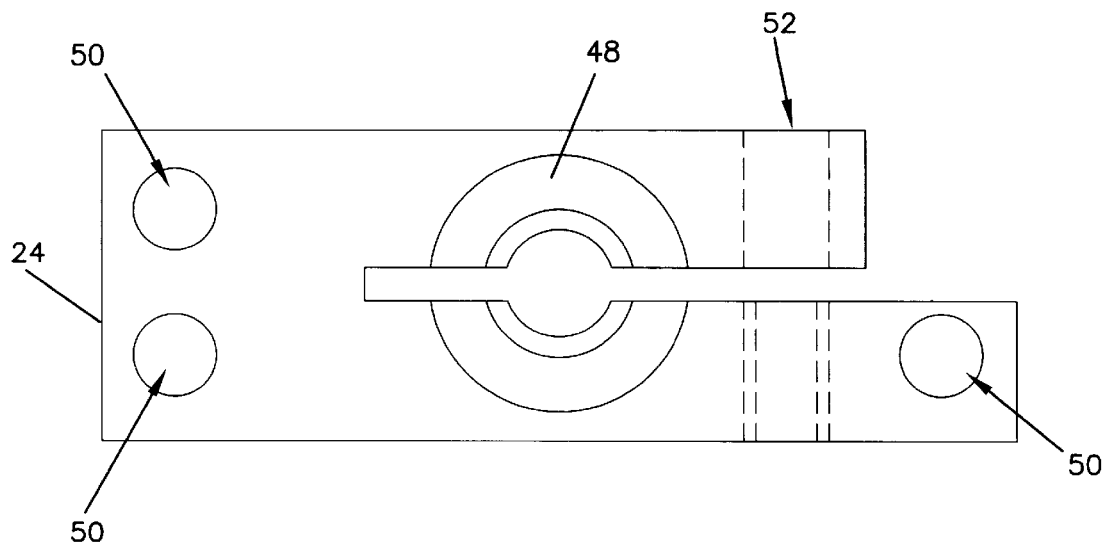
FIG. 7 illustrates a front view of the clamp used to clamp the infrared source within its housing.
Figure 8:
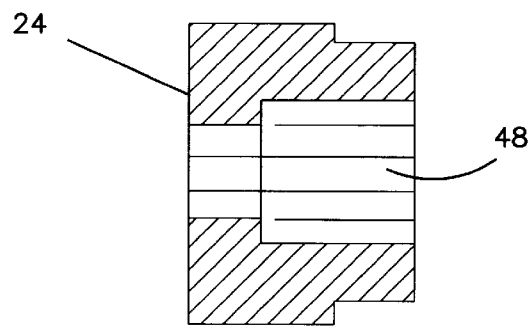
FIG. 8 illustrates a side view of the clamp of FIG. 7.

An important benefit of an infrared gas analyzer 10 so designed is that the infrared transmissive window 30 is shared by the detection volume 28 and the infrared energy source 25 and its housing 26. Similarly, the infrared transmissive window 32 is shared by the detection volume 28 and the infrared energy detector 16. Such a design is more optically efficient than designs using two windows because fresnel reflection losses from the multiple window surfaces are substantially reduced. Moreover, the optical path length is substantially shortened. Preferably, the infrared transmissive windows 30 and 32 are sealed in recessed features 40 and 44 provided in the sample cell 18, as shown in FIGS. 4–6. The infrared transmissive windows 30 and 32 are preferably secured and sealed in place by a gap filling, cyanoacrylate cement, and the sealed infrared transmissive windows 30 and 32 form the final seal on the gas path as well as providing protection for the infrared energy source 25 and the detection components of the infrared energy detector 16.

FIGS. 4–6 illustrate additional details of the sample cell 18 of the invention. As shown in FIG. 4, sample cell 18 includes a detection volume 28 which receives gas via a gas inlet 34 which receives tube fitting 20 and expels the gas via gas outlet 36 to tube fitting 22. The detection volume 28 preferably has smooth sides 38 to promote laminar flow of the received gas so as to provide a faster pneumatic response time. As shown in FIG. 4, sample cell 40 also includes a recessed area 40 on its bottom (detection) side for accepting the infrared transmissive window 32 of the infrared energy detector 16 so that the infrared transmissive window 32 may close off the detection side of the detection volume 28. The sample cell 18 receives mounting screws from the housing 26 in recesses 42. Similarly, as better shown in FIG. 6, sample cell 18 includes a recessed area 44 on its top (source) side for accepting the infrared transmissive window 30. Those skilled in the art will appreciate that this design permits the infrared energy source 25 to fill the entire field of view of the detection volume 28 and hence of the infrared energy detector 16.

After final assembly of the infrared gas analyzer 10 of the invention, the signal processing circuitry 14 is preferably calibrated by passing gases containing known concentrations of analyte(s) through the sample cell 18 and recording the response of the infrared energy detector 16. This data can be used to create a set of calibration coefficients which are preferably stored in a memory device, such as EPROM 15 illustrated in FIG. 2, which is physically mounted on the PCB 12 so that the calibration information cannot be separated from the infrared gas analyzer 10. The infrared gas analyzer 10 will remain calibrated so long as the physical relationships of the infrared energy source 25, sample cell 18, and infrared energy detector 16 are not disturbed.

Figure 9:
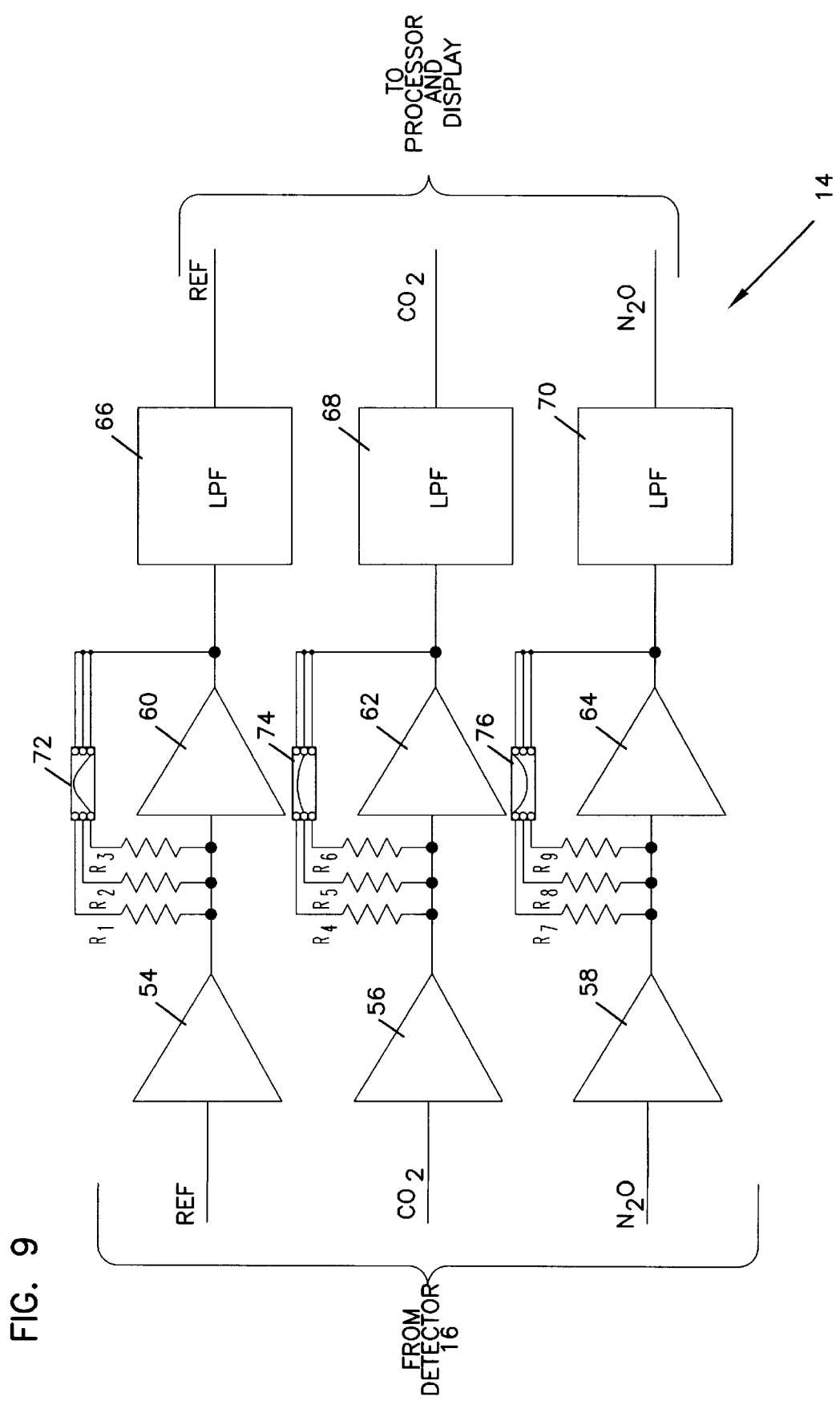
FIG. 9 illustrates a simplified version of the signal processing circuitry for selectively preamplifying and filtering the electrical signals provided from the infrared energy detector for each constituent channel.

FIG. 9 illustrates a simplified version of the signal processing circuitry 14 for selectively preamplifying and filtering the electrical signals provided in each channel from the infrared energy detector 16. As illustrated, the electrical signals from each channel of the infrared energy detector 16 (in this case, three channels are illustrated: $CO_2$, $N_2O$ and REF) are passed through respective buffers (54, 56, and 58) prior to application to a respective variable preamplifiers (60, 62, or 64) and then to respective low pass filters (66, 68, and 70). Then, as described below, the resulting electrical signals are then sent to a microprocessor (not shown) for calculation of the gas concentration for the gas measured in each channel. The results are then displayed to a technician on a display device (also not shown).

In accordance with another feature of the invention, the gain of the preamplifiers 60, 62, and 64 may be adjusted by manually adjusting PCB jumpers in the jumper connections 72, 74, and 76 in the respective feedback paths so that the feedback signal passes through a different one of the feedback resistors (R1–R9). In this manner, the gain of each of the preamplifiers 60, 62, and 64 may be set independent of the gains of the other preamplifiers in the other processing channels, which permits much looser tolerances on the performance specifications of the optical components (light source, detector, and analytical filters). Of course, independently adjustable gains make the analyzer more manufacturable and less costly than if components with tighter performance specifications were required.

The infrared gas analyzer 10 of the invention operates in a conventional manner. In particular, a sample gas stream taken from the patient's main respiratory airway is directed to sample cell 18 via tube fitting 20. The sample gas stream is typically pumped into the sample cell 18 using a downstream pneumatic device such as a pump (not shown). At sample cell 18, infrared light from the infrared energy source 25 passes through infrared transmissive window 30 into the detection volume 28 and through the gas to be analyzed, which, as noted above, flows through the sample cell in a smooth, laminar flow to improve pneumatic response time. The infrared light passing through the gas in the detection volume 28 is then selectively absorbed by the constituents in the gas stream, and the attenuated infrared light exits the detection volume 28 through infrared transmissive window 32 for detection by infrared energy detector 16. As described in U.S. Pat. No. 5,081,998, the infrared energy detector 16 typically contains filters for selectively filtering the attenuated infrared light at the respective characteristic frequencies of the different constituents. Infrared energy detector 16 also converts the received light into electrical signals which pass through the signal processing circuitry of FIG. 9 before being processed in a microprocessor (not shown) into values indicative of the concentrations of the respective measured constituents in the gas flow stream. This information is then presented to the technician via a display (also not shown).

As illustrated in FIG. 9, the signal processing performed on the raw detection signals from the infrared gas analyzer 10 generally comprises conditioning the signals using a single stage preamplifier with a variable fixed gain and a 20 Hz low pass filter. As noted above, the fixed gain is variable for each channel by manually adjusting a jumper in a jumper connector 72, 74, or 76 on the PCB 12.

As noted in U.S. Pat. No. 5,081,998, the infrared energy detector 16 may include a thermistor temperature sensor mounted directly underneath a thermopile substrate, the thermistor having a nominal impedance of, e.g., 20 KΩ at 25° C. The thermistor signal is typically buffered by an amplifier of the signal processing circuitry 14 and preferably can be measured at a pin of the PCB 12.

As also noted above, unit specific calibration coefficients are preferably stored in a memory, such as EPROM 15, on the PCB 12. By way of example, such calibration coefficients for a $CO_2$ and $N_2O$ infrared gas analyzer 10 may include the following:

| Coefficient | Definition |
|---|---|
| S/N | Serial Number |
| Rt | nominal thermistor series resistance |
| Tc1 ... Tc4 | 4 constants for the polynomial expansion of the temperature affect on $CO_2$ |
| Tn1 ... Tn4 | 4 constants for the polynomial expansion of the temperature affect on $N_2O$ |
| Coff | offset voltage of $CO_2$ channel |
| Noff | offset voltage of $N_2O$ channel |
| Roff | offset voltage of REF channel |
| Sc | $CO_2$/REF Span Factor |
| Sn | $N_2O$/REF Span Factor |
| Ac ... Hc | 8 constants for the polynomial expansion of $CO_2$ |
| An ... Hn | 8 constants for the polynomial expansion of $N_2O$ |

Software of a microprocessor of the signal processing circuitry 14 typically calculates the gas concentrations of the respective gas constituents as well as other values. For example, the microprocessor of the signal processing circuitry 14 may compute the concentrations of the measured gases (e.g., $CO_2$ and $N_2O$) by first computing the logarithms and cross product terms (where Ln denotes natural logarithm):

$$LC=Ln(Rc)$$

$$LN=Ln(Rn)$$

$$CP=LC*LN$$

and then computing the $CO_2$ concentration in mm Hg as follows:

$$CO_2=\{Ac+(Bc*LC)+(Cc*LC^2)+(Dc*LC^3)+(Ec*LN)+(Fc*LN^2)+(Gc*LN^3)+(Hc*CP)\}*C02TCF$$

where Ac ... Hc are unit specific constants stored in the EPROM 15, and computing the $N_2O$ concentration in mm Hg as follows:

$$N_2O=\{An+(Bn*LN)+(Cn*LN^2)+(Dn*LN^3)+(En*LC)+(Fn*LC^2)+(Gn*LC^3)+(Hn*CP)\}*N20TCF$$

where An ... Hn are unit specific constants stored in the EPROM 15. Preferably, the processing of the raw detection signals by the infrared gas analyzer 10 of the invention incorporates the gas concentration computation techniques described by the present inventors in the afore-mentioned patents, including U.S. Pat. No. 5,281,817, the contents of which are hereby incorporated by reference in their entirety.

It will be appreciated by those skilled in the art that the foregoing has set forth the presently preferred embodiment of the invention and an illustrative embodiment of the invention but that numerous alternative embodiments are possible without departing from the novel teachings of the invention. Accordingly, all such modifications are intended to be included within the scope of the appended claims.

We claim:

1. An infrared gas analyzer for detecting the concentration of a gaseous component of a substantially gaseous flow stream provided via an airway, comprising:

an infrared energy detector which converts received incident radiation into at least one electrical signal representative of the received incident radiation, said infrared energy detector having a first infrared transmissive window on a detection side thereof through which said incident radiation passes for detection;

a sample cell mounted on said detection side of said infrared energy detector such that said first infrared transmissive window of said infrared energy detector is shared with said sample cell on one side thereof, said sample cell receiving at least a portion of said substantially gaseous flow stream and directing said portion to a detection volume having a smooth surface and a low swept volume which promote laminar flow of said gaseous flow stream through said sample cell; and a source of infrared energy mounted on a side of said sample cell opposite said infrared energy detector so as to emit infrared energy through a second infrared transmissive window which is shared by said source and a side of said detection volume opposite said one side, through said detection volume for absorption by said gaseous component, and through said first infrared transmissive window for detection by said infrared energy detector, whereby said infrared energy from said source passes through a single infrared transmissive window to enter said sample cell on said other side of said sample cell and exits said sample cell through a single infrared transmissive window on said one side of said sample cell for detection.

2. An analyzer as in claim 1, further comprising a circuit board containing signal processing circuitry which processes said at least one electrical signal, wherein said infrared energy detector is mounted directly onto said circuit board.

3. An analyzer as in claim 2, wherein said infrared energy detector has a least two output channels and said signal processing circuitry includes amplifier circuitry for each output channel of said infrared energy detector, the amplifier circuitry for each output channel including a jumper connector whereby a gain of each output channel is set independent of a gain of each other output channel by adjusting a position of said jumper connector.

4. An analyzer as in claim 2, wherein said signal processing circuitry includes a memory containing calibration coefficients for accounting for differential absorption effects of said infrared energy detector, sample cell, infrared energy source, and said first and second infrared transmissive windows.

5. An analyzer as in claim 1, wherein said infrared energy source is mounted on said sample cell opposite said infrared energy detector so as to completely fill a field of view of said infrared energy detector.

6. An analyzer as in claim 1, further comprising a housing for said infrared energy source and a clamp which clamps said infrared energy source within said housing adjacent said second infrared transmissive window.

7. A method of manufacturing an infrared gas analyzer which detects the concentration of a gaseous component of a substantially gaseous flow stream provided via an airway, comprising the steps of:

mounting an infrared energy detector onto a circuit board containing signal processing circuitry which processes electrical signals output by said infrared energy detector in response to received incident radiation;

mounting a sample cell on a detection side of said infrared energy detector such that said sample cell and said infrared energy detector share a first infrared transmissive window on one side of said sample cell through which said incident radiation passes for detection, whereby said sample cell, when mounted, receives at least a portion of said substantially gaseous flow stream and directs said portion to a detection volume having a smooth surface and a low swept volume which promote laminar flow of said gaseous flow stream through said sample cell; and mounting a source of infrared energy on a side of said sample cell opposite said infrared energy detector such that said infrared energy source and said sample cell share a second infrared transmissive window through which infrared energy from said infrared energy source passes into said detection volume for absorption by said gaseous component, whereby, during use of said infrared gas analyzer, said infrared energy from said source passes through a single infrared transmissive window to enter said sample cell on said other side of said sample cell and exits said sample cell through a single infrared transmissive window on said one side of said sample cell for detection.

8. A method as in claim 7, wherein said infrared energy detector has at least two output channels, comprising the further step of setting a gain of each output channel of said infrared energy detector independent of a gain of each other output channel by adjusting a position of a jumper connector in amplifier circuitry in said signal processing circuitry for each output channel.

9. A method as in claim 7, comprising the further step of calibrating said signal processing circuitry using calibration coefficients stored in a memory in said signal processing circuitry on said circuit board.

10. A method as in claim 7, wherein said infrared energy source mounting step includes the step of mounting said infrared energy source on said sample cell opposite said infrared energy detector so as to completely fill a field of view of said infrared energy detector.

11. A method as in claim 7, wherein said infrared energy source mounting step includes the step of clamping said infrared energy source within a housing for said infrared energy source such that said infrared energy source is adjacent said second infrared transmissive window.

* * * * *

UNITED STATES PATENT AND TRADEMARK OFFICE
CERTIFICATE OF CORRECTION

PATENT NO. : 5,932,877
DATED : August 3, 1999
INVENTOR(S) : James R. Braig and Daniel S. Goldberger It is certified that error appears in the above-identified patent and that said Letters Patent is hereby corrected as shown below:

Column 2, line 7, after "detectors", the next word "Conventional" should start a new paragraph.

Signed and Sealed this

Twenty-first Day of March, 2000

Attest:

Q. TODD DICKINSON

Attesting Officer

Commissioner of Patents and Trademarks